United States Patent

Huang et al.

[11] Patent Number: 5,567,857
[45] Date of Patent: Oct. 22, 1996

[54] FLUOROALKYLETHOXYLATE COMPOSITIONS HAVING ENHANCED WATER SOLUBILITY

[75] Inventors: Hsu-Nan Huang, Newark; Robert A. Halling, Wilmington, both of Del.

[73] Assignee: E. I. Du Pont de Nemours and Company, Wilmington, Del.

[21] Appl. No.: 263,091

[22] Filed: Jun. 21, 1994

[51] Int. Cl.$^6$ .................................................. C07C 43/11
[52] U.S. Cl. ............................................................. 568/615
[58] Field of Search ................................................ 568/615

[56] References Cited

U.S. PATENT DOCUMENTS 3,948,668  4/1976  Hayek et al. .............................. 106/22

Primary Examiner—Gary Geist
Assistant Examiner—Dwayne C. Jones

[57] ABSTRACT

Mixture of the compounds: $F(CF_2)_m—(CH_2)_n—(OCH_2CH_2)p—OH$ wherein m=2 and about 20, but in at least 5 weight % of molecules m is 8 or higher or mixtures of the same, but in no more than 5 weight % of the molecules is m equal to 14 or higher or mixtures of the same; n=1 to 3; & p=1 to 40, but the mixture has an average p=8 to 17.

11 Claims, No Drawings

FLUOROALKYLETHOXYLATE COMPOSITIONS HAVING ENHANCED WATER SOLUBILITY

FIELD OF THE INVENTION

The present invention relates to novel perfluoroalkylethoxylate compositions prepared by the reaction of a fluorinated alcohol or fluorinated alcohol mixture with ethylene oxide, said perfluoroalkylethoxylate compositions having beneficial properties including enhanced solubility in water.

BACKGROUND OF THE INVENTION

Perfluoroalkylethoxylate having the following structure are known:

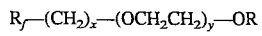

$$R_f-(CH_2)_x-(OCH_2CH_2)_y-OR$$

wherein $R_f$ is one or more perfluoroalkyl groups having between 2 and 30 carbon atoms; x is 1 to 3; y is 1 to 200; and R is hydrogen, alkyl or aryl. They can be prepared by the reaction of one or more pefluoroalkyl alkanols with ethylene oxide in the presence of a catalyst. They have several important industrial applications, including use as nonionic fluorosurfactants in the manufacture of PVC films, electrochemical cells, and photographic coatings. The useful properties of such fluoroalkylethoxylates are strongly influenced by their structural features, e.g. the size and chemical structure of the $R_f$ group, whether the composition comprises molecules having $R_f$ groups of the same length or a mixture of molecules having $R_f$ groups of different lengths, and the average number (y) and distribution of oxyalkylene groups. Fluoroalkylethoxylate compositions comprising a mixture of molecules having linear perfluoroalkyl groups of different length (for example, the commercial product ZONY® FSN marketed by E. I. du Pont de Nemours and Company) have distinctive surfactant properties, and can be considerably less expensive to manufacture than single isomer analogs. Unfortunately, such known mixtures of fluoroalkylethoxylates suffer from several deficiencies, including solubility in water of less than 10 weight percent and the tendency to form solutions containing sediment. (The term "solubility" as used in this specification is defined as the weight percent of fluoroalkylalkoxylate which may be added to a solvent such as water, or a water-organic solvent mixture at 25° C. without causing the formation of turbidity or sediment).

It is more convenient and economical to manufacture, store, and ship fluoroalkylalkoxylate in a solution of higher concentration, typically at about 40 percent by weight. In order to achieve this high solution concentration, known fluoroalkylalkoxylates must be dissolved in an organic solvent, such as isopropyl alcohol (IPA), or in a solvent mixture comprising water in combination with one or more of such organic solvents. However, the resulting solution may be flammable or have increased toxicity, and thus be more difficult and expensive to ship and use safely. In addition, the users of said fluoroalkylalkoxylate solutions frequently must remove the organic solvent during their manufacturing operations; this can be expensive and result in increased worker safety and environmental hazards. Even when dissolved in organic solvent mixtures, known fluoroalkylalkoxylates tend to form sediments. Such sediments are not easily filterable, and they tend to form continuously over time, which makes it impractical to remove the sediments from fluoroalkylalkoxylate solutions before shipment to the user. There are other fluoroalkylalkoxylates disclosed in the prior art which have higher water solubility, e.g. those having a large average number of the hydrophilic oxyalkylene groups, typically greater than about 18 such groups. Another example is Fluorotenside FT 219 marketed by Bayer AG; however, the structures of that product and related compositions incorporate additional hydrophilic functional groups, such as sulfonylamido linkages. In addition, a high degree of alkoxylation may result in the fluoroalkylalkoxylate composition forming a gel during preparation that makes them difficult or impossible to use.

A fluoroalkylalkoxylate having good nonionic surfactant properties and capable of being supplied in water solution at concentrations of at least 40 percent by weight without the formation of sediment would have great utility and value in the marketplace.

BRIEF SUMMARY OF THE INVENTION

The present invention relates to novel fluoroalkylethoxylate compositions comprising the reaction product of a mixture of perfluoroalkylalkanols with ethylene oxide in the presence of a suitable catalyst, said fluoroalkylethoxylate compositions being soluble in water up to concentrations of about 50 percent by weight at 25° C., and said fluoroalkylethoxylate compositions forming water solutions having no sediment.

DETAILED DESCRIPTION OF THE INVENTION

The present invention relates more particularly to novel compositions comprising a mixture of fluoroalkylethoxylates having the general formula:

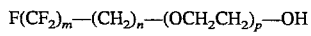

$$F(CF_2)_m-(CH_2)_n-(OCH_2CH_2)_p-OH$$

wherein $F(CF_2)_m-$ is a linear perfluoroalkyl group;

m is an integer in the range between 2 and about 20, provided that the mixture contains at least 5 weight percent of molecules in which m is 8 or higher or mixtures of the same, but in no more than 5 weight percent of the molecules is m equal to 14 or higher or mixtures of the same;

n is an integer in the range between 1 and 3; and p is an integer in the range between 1 and about 40, provided that the distribution of molecules in said mixture has an average p in the range between 8 and 17.

In respect of the length of the linear fluoroalkyl group in the molecules of the mixture (m), the compositions of the present invention comprise mixtures of molecules having m in the range between 2 and about 20. The percentage of molecules in the mixture having m equal to 8 or higher, or mixtures of the same, must be 5% by weight or greater; provided that no more than 5 weight percent of the molecules have m equal to 14 or higher or mixtures of the same; otherwise dilute water solutions of the fluoroalkylethoxylate will not have the beneficial property of relatively constant surface tension in the concentration range between 0.1 and 0.01 percent by weight of fluoroalkylethoxylate. The percentage of molecules in the fluoroalkylethoxylate mixture having m of 14 or higher, or mixtures of the same, must be 5 percent by weight or lower; otherwise water solutions of the fluoroalkylethoxylate will contain sediment and be turbid.

Concerning the number of the linear alkylene linking groups, n, the compositions of the present invention comprise molecules having n equal to 1, 2, 3, or mixtures of the same. In the preferred embodiment n is 2.

With regard to the degree of ethoxylation, p, the compositions of the present invention comprise mixtures having a distribution of fluoroalkylethoxylate molecules having different numbers of oxyethylene units. This distribution may include molecules having from 1 to 40 oxyethylene units (p) clustered about a peak value of p and tapering off at higher and lower values of p. The distribution of p will have an average over all molecules in the mixture, referred to herein as the average degree of ethoxylation ($P_{average}$) in the range between about 8 and about 17. For a mixture having the distribution of fluoroalkyl groups defined hereinbelow, if $P_{average}$ is lower than about 8 the composition will have low water solubility. Alternatively, if the mixture has $P_{average}$ greater than about 17, water solutions of the mixture will not have adequate surface tension reduction to be useful as nonionic fluorosurfactants.

In a preferred embodiment, the compositions comprise mixtures having $P_{average}$ in the range between about 12 and about 17. In addition to having enhanced solubility in water and adequate surfactant properties, water solutions of the fluoroalkylethoxylate compositions in which $P_{average}$ is between about 12 and 17 will possess the added advantage of upper cloud points (UCP) near 100° C. UCP refers to the temperature at which the fluorosurfactant forms a separate phase leading to higher solution surface tension and often cloudiness. A higher temperature UCP thus affords an enhanced temperature range of utility for use of the fluoroalkylethoxylate composition. Fluoroalkylethoxylate compositions of the present invention having $P_{average}$ lower than about 12 have much reduced UCP temperatures.

The water solution properties that make the fluoroalkylethoxylate compositions of the present invention particularly useful as nonionic surfactants include reduced solution surface tension and small variation of solution surface tension with changing fluoroalkylethoxylate concentration. In order to be commercially useful, water solutions of surfactant at a concentration in the range between 0.01 and 0.1 percent by weight should have a surface tension below 30 dyne/cm. When the compositions of the present invention are dissolved in water and diluted to concentrations in the range between 0.01 and 0.1 percent fluoroalkylethoxylate by weight, the resulting solutions have surface tensions in the range between 16 and 24 dyne/cm. For certain compositions having a lower average degree of ethoxylation in the range between 8 and 14, adequately low solution surface tensions may be achieved even at concentrations as low as 0.001 percent fluoroalkylethoxylate by weight.

In addition, water solutions of the compositions of the present invention exhibit only small changes in solution surface tension with changes in fluoroalkylethoxylate concentration over the range of 0.01 to 0.1 percent by weight. The actual variation in solution surface tension across this fluoroalkylethoxylate concentration range is typically near zero, and for none of the compositions of the present invention is it greater than about 1 dyne/cm. This contrasts with many other fluorinated surfactants for which much larger changes in solution surface tension are observed with varying surfactant concentration across this range. This is a significant advantage in the use of the compositions of the present invention in industrial applications since the user has much greater flexibility relative to surfactant solution concentration in preparing solutions having a low, uniform surface tension. This results in simpler and faster processing operations with fewer process upsets due to solution surface tension variation outside of operating ranges. This factor is especially important in large, continuous commercial operations in which solutions having low and uniform surface tension need to be prepared quickly.

The fluoroalkylethoxylate compositions of the present invention are prepared by the reaction of a suitable fluorinated alcohol mixture with ethylene oxide in the presence of an appropriate catalyst in accordance with the following equation:

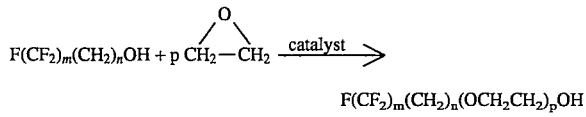

$$F(CF_2)_m(CH_2)_nOH + p\ CH_2\!-\!CH_2 \xrightarrow{\text{catalyst}}$$

$$F(CF_2)_m(CH_2)_n(OCH_2CH_2)_pOH$$

wherein m, n, and p have the values described above. The catalyst is a mixed system comprising an alkali metal borohydride in combination with at least one source of iodine selected from elemental iodine, an alkali metal iodide, or an alkaline earth metal iodide. The fluorinated alcohols useful as reactants in the process are well known; e.g. see U.S. Pat. No. 5,097,090 and patents cited in Col. 1 thereof (the USPTO file of that patent shows that "478,760" in Col. 1, line 19, should be "4,478,760"). Thus they may be prepared by methods known in the art, such as by the telomerization of tetrafluoroethylene in the presence of suitable catalysts followed by ethylation to afford fluorinated alcohols having n equal to 2. The distribution of fluoroalkyl groups (i.e. distribution of m) in the fluoroalkylethoxylate product mixture will closely approximate the distribution of fluoroalkyl groups in the starting fluorinated alcohol mixture, and so the alcohol mixture used should be chosen to be close to that desired in the fluoroalkylethoxylate product. In a preferred embodiment, the fluoroalkylethoxylates are derived from mixtures of fluorinated alcohols which are prepared by telomerization of TFE and which have a B distribution of m in the following ranges:

| m | percent by weight in mixture |
|---|---|
| 6 and lower | 0–70 |
| 8 | 20–60 |
| 10 | 5–40 |
| 12 | 1–25 |
| 14 and higher | 0–5 |

In a more preferred embodiment, the fluoroalkylethoxylates are derived from mixtures of fluorinated alcohols which are prepared by telomerization of TFE and which have a distribution of m in the following ranges:

| m | percent by weight in mixture |
|---|---|
| 6 and lower | 40–65 |
| 8 | 20–40 |
| 10 | 5–20 |
| 12 | 1–10 |
| 14 and higher | <3 |

The latter distribution is more preferred because it is similar to that produced in the commercial manufacture of these perfluoroalkyl ethanols, making them a more economical ingredient for the preparation of the fluoroalkylethoxylates of the present invention.

Alkali metal borohydrides are suitable for use in the catalyst system used in preparing the compositions of the present invention, e.g. sodium borohydride, potassium borohydride, and lithium borohydride, with sodium borohydride being preferred. The mole ratio of alkali metal borohydride to fluorinated alcohol can vary widely. Normally the mole ratio will range between about 0.005 and 0.25 or higher, the upper limit being imposed only by practical considerations such as the cost of excessive borohydride use, contamination of product and waste streams with excess borohydride, and potential difficulty in controlling the rate of the exothermic alkoxylation reaction. The optimum mole ratio of borohydride to fluorinated alcohol may be determined by standard experimental methods familiar to those skilled in the art of alcohol alkoxylation reactions, and will be affected by such factors as the structures of the perfluoroalkyl alkanol, and the temperature, pressure and cooling efficiency of the reaction equipment. For the reaction of the above-described fluorinated alcohol mixtures with ethylene oxide at 130° C. to 145° C. under atmospheric pressure, the preferred mole ratio of borohydride to fluorinated alcohol is in the range between about 0.025 and about 0.1.

Iodine sources suitable for use in the catalyst system include lithium iodide, sodium iodide, potassium iodide, calcium iodide, and elemental iodine. The use of iodine or sodium iodide or a mixture of the same is preferred. The mole ratio of iodine source to alkali metal borohydride is in the range between about 0.1:1 and about 300:1. The optimum mole ratio of iodine source to borohydride may be determined by standard experimental methods familiar to those skilled in the art. For the reaction of the above described fluorinated alcohol mixtures with ethylene oxide at 130° C. to 145° C. under atmospheric pressure, the preferred mole ratio of iodine source to borohydride is in the range between 0.1:1 and about 0.5:1, and the most preferred mole ratio is in the range between about 0.1:1 and 0.3:1. At high levels of iodine source relative to borohydride, the alkoxylation reaction may be inhibited and the reaction rate slower.

Inert materials or solvents may also be present during the reaction, although in the preferred embodiment both the ethylene oxide and the fluorinated alcohol or fluorinated alcohol mixture are reacted in neat form. The process can be carried out at temperatures of from about 90° C. to about 200° C. For practical purposes, commercial operation of the process will be carried out in the temperature range between about 120° C. and about 170° C. The process can be carried out at ambient atmospheric pressure, however pressures above or below ambient can be used as desired. It is essential only that sufficient pressure be used to maintain the alcohols present in the liquid phase during the ethoxylation reaction. Normally, pressures of up to about 100 pounds per square inch gauge (psig) can be used, the upper limit being imposed primarily by convenience, cost, and the cooling efficiency of the reaction equipment. Reaction pressures in the range between ambient atmospheric pressure and about 50 psig are preferred, with operation in the range between about 20 and about 50 psig especially preferred.

The process for preparing the compositions of the present invention allows much flexibility in the operation of the process. The alkali metal borohydride and iodine source may be added to the fluorinated alcohol prior to, during, or after the addition of the ethoxylating agent. The two catalysts may be added at different times in the course of the alkoxylation, although in the absence of other catalytic species the reaction will not proceed at an appreciable rate until both catalysts are present. In the preferred embodiment, the fluorinated alcohol or mixture is mixed with the alkali metal borohydride and iodine source prior to addition of the ethoxylating agent.

The fluoroalkylethoxylate mixture prepared by the aforementioned process can be mixed with water up to a fluoroalkylethoxylate concentration approaching 50 percent by weight without the formation of sediments or turbidity. Such mixtures should be stable indefinitely under typical storage and shipment conditions without experiencing bulk phase separation or sediment formation.

The following Examples are given in further illustration of the invention but not by way of limitation. Unless otherwise indicated, percentages are by weight. Test methods used in the Examples are given below.

PROCEDURE FOR DETERMINATION OF SURFACTANT WATER SOLUBILITY

The following Examples are given in further illustration of the invention but not by way of limitation. Unless otherwise indicated, percentages are by weight. Test methods used in the Examples are given below.

PROCEDURE FOR DETERMINATION OF SURFACTANT WATER SOLUBILITY

The water solubility of the fluoroalkylethoxylate compositions was determined by slowly adding the fluoroalkylethoxylate to 60 grams of distilled water at 25° C. with agitation provided by a magnetic stirring apparatus. The mass of fluoroalkoxylate added was measured during the addition, and the addition was continued until the development of solution turbidity was observed. The solubility is given by the weight percent of fluoroalkoxylate that may be added to the water before development of turbidity is observed.

PROCEDURE FOR DETERMINATION OF SOLUTION SURFACE TENSION

All surface tension measurements were made using a University of Texas model 500 Spinning Drop Interfacial Tensiometer. A solution of fluoroalkylethoxylate was prepared in distilled water and diluted to the desired concentration. The solution surface tension was then measured following the standard operating instructions supplied with the tensiometer.

PROCEDURE FOR DETERMINATION OF UPPER CLOUD POINT

Upper cloud point determinations were performed on fluoroalkylethoxylate solutions using a modified version of ASTM standard method D2024-65. A 1 gram sample of fluoroalkoxylate was dissolved in 100 milliliters of deionized water in a beaker. The beaker was placed on a hot plate and the solution was stirred and gradually heated until solution cloudiness was observed, the temperature of this occurrence being recorded as T1. The beaker was then removed from the hot plate and allowed to cool with continued stirring until the cloudiness disappeared, the temperature of this occurrence being recorded as T2. The upper cloud point was calculated as the average of T1 and T2 rounded to the nearest degree Celsius.

EXAMPLE 1

To a 250 milliliter flask under an inert nitrogen atmosphere at 1 atmosphere pressure and equipped with a dry ice condenser and gas inlet was charged 60 grams (approximately 0.145 mole) of a mixture composed of 54% $F(CF_2)_6CH_2CH_2OH$, 33% $F(CF_2)_8CH_2CH_2OH$, approximately 9.5% $F(CF_2)_{10}CH_2CH_2OH$, approximately 3.5% $F(CF_2)_{12}CH_2CH_2OH$, and less than 0.1%

$F(CF_2)_mCH_2CH_2OH$ wherein m is 14 or greater. To that mixture was added quickly rose to and remained at about 140° C. The reaction mixture was then allowed to cool to room temperature. After removing the dry ice from the condenser, the reaction mixture was purged with nitrogen for 12 hours to remove any residual ethylene oxide. The product was then neutralized with 0.36 grams (0.04 mole) of acetic acid. The yield of product was 95% (based on weight gain). The product was $F(CF_2)_mCH_2CH_2(OCH_2CH_2)_pOH$, wherein m is an integer in the range of 4 to 14; n is an integer in the range of 1 to 30 with an average of about 12. A clear, one phase solution was obtained when 40 g of this product was mixed with 60 g of water at room temperature.

By way of contrast, the water solubilities of several commercial fluoroalkylalkoxylates are shown in Table 1, from which it can be seen that they have very low solubilities in water, generally lower than 8 percent by weight.

TABLE 1

| Water Solubility of Commercial Fluoroalkylalkoxylates | | |
|---|---|---|
| Manufacturer | Product | Water-Solubility @ 25° C. |
| Hoechst | Afilon OTN | 0.1 |
| Ciba-Geigy | S-107B | 0.1 |
| Asahi Glass | S-141 | <5 |
| DuPont | Zonyl FSN-100 | 8 |
| Daikin | DS-401 | <1 |

EXAMPLES 2–6 & Control A & B

The fluoroalkylethoxylate compositions of Examples 2 through 6 and Controls A and B were prepared in a manner similar to Example 1 as described in Table 2. The fluorinated alcohol mixture employed for each of Examples 2 through 6 and Controls A and B was similar to that of Example 1. The water solubilities and water solution characteristics of the fluoroalkylethoxylate product mixtures of Examples 2 through 6 and Controls A and B are shown in Table 3.

TABLE 2

| Reaction Conditions for Examples 2–6 & Controls A & B | | | | | | |
|---|---|---|---|---|---|---|
| Example [Control] | mole $R_fOH$ | mole EO | mole NaI | mole $I_2$ | mole $NaBH_4$ | Temp, °C. | Time, h |
| [A] | 0.144 | 0.979 | 0.0007 | 0 | 0.006 | 143 | 4.7 |
| [B] | 0.144 | 1.044 | 0.0007 | 0 | 0.006 | 145 | 5.0 |
| 2 | 0.144 | 1.166 | 0.0007 | 0 | 0.006 | 145 | 4.4 |
| 3 | 0.140 | 1.428 | 0.003 | 0.001 | 0.006 | 149 | 5.2 |
| 4 | 0.150 | 1.815 | 0.003 | 0.002 | 0.006 | 138 | 4.8 |
| 5 | 0.180 | 2.484 | 0.004 | 0.002 | 0.007 | 143 | 6.3 |
| 6 | 0.140 | 2.436 | 0.003 | 0.001 | 0.006 | 145 | 4.5 |

TABLE 3

| Water Solubility and Solution Characteristics of Fluoroalkylethoxylate Products of Examples 2–6 & Controls A & B | | | |
|---|---|---|---|
| Example [Control] | Avg EO Number (Paverage) | Water Solubility (wt. percent) | Water Solution Turbidity |
| [A] | 6.8 | <1 | 2 liq. phases |
| [B] | 7.2 | <1 | 2 liq. phases |
| 2 | 8.1 | >40 | Clear |
| 3 | 10.2 | >40 | Clear |
| 4 | 12.1 | >40 | Clear |
| 5 | 13.8 | >40 | Clear |
| 6 | 17.4 | >40 | Clear |

The data set forth in Table 3 indicate that only fluoroalkylethoxylate compositions having an average EO number of 8 or greater exhibit enhanced water solubility.

Samples of the fluoroalkylethoxylate products from Examples 2 through 6 were dissolved in water and diluted to final concentrations of 0.1, 0.01, and 0.001 percent fluoroalkylethoxylate by weight. The surface tensions of these solutions were then determined, and the results are shown in Table 4 along with upper cloud point data for these products.

TABLE 4

| Water Solution Surface Tension and Upper Cloud Point for Fluoroalkylethoxylate Products of Examples 2–6 | | | | | |
|---|---|---|---|---|---|
| Example | Avg EO Number (Paverage) | Water Solution Surface Tension (dyne/cm) at indicated concentration | | | UCP, °C. |
| | | 0.1 wt % | 0.01 wt % | 0.001 wt % | |
| 2 | 8.1 | 16 | 16 | 20 | no data |
| 3 | 10.2 | 19 | 19 | 27 | 80 |
| 4 | 12.1 | 21 | 21 | 26 | >98 |
| 5 | 13.8 | 22 | 23 | 29 | >99 |
| 6 | 17.4 | 28 | 29 | 35 | >100 |

The data of Table 4 show that the surface tensions of solutions of the fluoroalkoxylate composition are constant across the concentration range of 0.01 to 0.1 percent by weight for all shown compositions. The solution surface tension does increase with increasing average EO number until the surface tension approaches the upper useful limit for fluorosurfactants of 30 dyne/cm when the EO number is 17.4 as in Example 6. In addition, it may be seen that the upper cloud points of the fluoroalkoxylates also increase with increasing EO number, approaching values near 100° C. when the average EO number is 12 or higher. Even at an average EO number of 8 as in Example 2, however, the UCP is sufficiently high to be useful for many applications.

EXAMPLE 7 & Controls C & D

The fluoroalkylethoxylate compositions of Example 7 and Controls C & D were prepared in a manner similar to Example 1 as described in Table 5. The fluorinated alcohol mixture employed for each of Example 9 and Controls C & D was similar to that of Example 1, except that the mixture was spiked with samples of pure $F(CF_2)_mCH_2CH_2OH$ where m is 14, 16, and 18 to give the concentrations of these compounds as indicated in the key to Table 5. Water solutions of the fluoroalkylethoxylates of Examples 7 and Controls C & D were prepared by mixing grams of ethoxylate in 60 grams of water. The resulting characteristics of these solutions are described in Table 6.

TABLE 5

| Reaction Conditions for Example 7 & Controls C & D | | | | | | | |
|---|---|---|---|---|---|---|---|
| Example [Control] | mole $R_fOH$ | mole EO | mole NaI | mole $I_2$ | mole $NaBH_4$ | Temp, °C. | Time |
| 7[a] | 0.139 | 1.751 | 0.003 | 0.001 | 0.006 | 145 | 4.2 |
| [C][b] | 0.136 | 1.822 | 0.003 | 0.001 | 0.005 | 145 | 5.5 |
| [D][b] | 0.132 | 2.112 | 0.0007 | 0 | 0.005 | 145 | 7.8 |

(a) composition same as Example 1, but spiked to give:
$F(CF_2)_{14}CH_2CH_2OH$ 3.0%
$F(CF_2)_{16}CH_2CH_2OH$ 1.4%
$F(CF_2)_{18}CH_2CH_2OH$ 0.5%
(b) composition same as Example 1, but spiked to give:
$F(CF_2)_{14}CH_2CH_2OH$ 3.6%

TABLE 5-continued

Reaction Conditions for Example 7 & Controls C & D

| Example [Control] | mole $R_fOH$ | mole EO | mole NaI | mole $I_2$ | mole $NaBH_4$ | Temp, °C. | Time |
|---|---|---|---|---|---|---|---|
| $F(CF_2)_{16}CH_2CH_2OH$ 1.6% | | | | | | | |
| $F(CF_2)_{18}CH_2CH_2OH$ 0.6% | | | | | | | |

TABLE 6

Water Solution Characteristics of Fluoroalkylethoxylate Products of Example 7 & Controls C & D

| Example [Control] | Avg EO Number (Paverage) | Water Solution Sediment | Water Solution Turbidity |
|---|---|---|---|
| 7 | 12.6 | No | Clear |
| [C] | 13.4 | Yes | Cloudy |
| [D] | 16.0 | Yes | Cloudy |

It is apparent from the data of Table 6 that the enhanced water solubility of the fluoroalkoxylate compositions of the present invention is diminished when the composition includes greater than 5% of molecules having n equal to 14 and higher as in Controls C & D.

EXAMPLE 8 & CONTROL E

The fluoroalkylethoxylate compositions of Example 8 & Control E were prepared in a manner similar to Example 1 as described in Table 7. The fluorinated alcohol mixture employed for Control E consisted of 97% $F(CF_2)_6CH_2CH_2OH$ and 3% $F(CF_2)_8CH_2CH_2OH$ by weight, while that employed for Example 8 consisted of 95% $F(CF_2)_6CH_2CH_2OH$ and 5% $F(CF_2)_8CH_2CH_2OH$ by weight. The average degree of ethoxylation ($P_{average}$) was 12.8 and 12.6, respectively. The fluoroalkylethoxylate products of both Example 8 and Control E were soluble in water to greater than 40 percent by weight, said solutions having no sediment and being clear. Samples of each fluoroalkylethoxylate product were dissolved in distilled water and diluted to concentrations of 0.1 and 0.01 percent fluoroalkylethoxylate by weight. The surface tensions of the resulting solutions were measured, and are shown in Table 8.

TABLE 7

Reaction Conditions for Example 8 & Control E

| Example [Control] | mole $R_fOH$ | mole EO | mole NaI | mole $I_2$ | mole $NaBH_4$ | Temp, °C. | Time |
|---|---|---|---|---|---|---|---|
| [E]$^a$ | 0.132 | 1.70 | 0.003 | 0.001 | 0.005 | 145 | 5.5 |
| 8$^b$ | 0.139 | 1.75 | 0.003 | 0.001 | 0.006 | 145 | 4.2 |

$^a$fluorinated alcohol mixture composed of 97% $F(CF_2)_6CH_2CH_2OH$ and 3% $F(CF_2)_8CH_2CH_2OH$;
$^b$fluorinated alcohol mixture composed of 95% $F(CF_2)_6CH_2CH_2OH$ and 5% $F(CF_2)_8CH_2CH_2OH$.

TABLE 8

Water Solution Surface Tension for Fluoroalkylethoxylate Products of Example 8 And Control E

| Example [Control] | Weight Percent | Water Solution Surface Tension (dyne/cm) at indicated concentration | |
|---|---|---|---|
| | | 0.1 wt % | 0.01 wt % |
| [E] | $F(CF_2)_8CH_2CH_2OH$ 3 | 23 | 29 |

TABLE 8-continued

Water Solution Surface Tension for Fluoroalkylethoxylate Products of Example 8 And Control E

| Example [Control] | Weight Percent | Water Solution Surface Tension (dyne/cm) at indicated concentration | |
|---|---|---|---|
| | | 0.1 wt % | 0.01 wt % |
| 8 | $F(CF_2)_8CH_2CH_2OH$ 5 | 24 | 24 |

It is apparent from Table 8 that the composition of Control E, which has 97% by weight of molecules wherein n is below 8, does not exhibit constant surface tension with varying water solution concentration between 0.01 and 0.1 percent by weight. However, when the composition is adjusted in Example 8 to one having only 95% of molecules with n below 8, constant surface tension across this concentration range is again observed.

We claim:

1. An improved composition comprising a mixture of fluoroalkylethoxylates having the general formula:

$$F(CF_2)_m-(CH_2)_n-(OCH_2CH_2)_p-OH$$

wherein $F(CF_2)_m-$ is a linear perfluoroalkyl group;

m is an integer in the range between 2 and about 20;

n is an integer in the range between 1 and 3; and p is an integer in the range between 1 and about 40;
wherein the improvement comprises solubility in water at a concentration of at least 40% by weight without formation of sediment, by the presence of at least 5 weight percent of molecules in which m is 8 or higher or mixtures of the same, but in no more than 5 weight percent of the molecules is m equal to 14 or higher or mixtures of the same, and the distribution of molecules in said mixture has an average p in the range of between 8 and 17.

2. The composition of claim 1 wherein n is 2.

3. The composition of claim 1 wherein the average of p in the molecular distribution of the mixture is in the range between about 12 and about 17.

4. The composition of claim 3 wherein n is 2.

5. A process for preparing a mixture of fluoroalkylethoxylates having the general formula:

$$F(CF_2)_m-(CH_2)_n-(OCH_2CH_2)_p-OH$$

wherein $F(CF_2)_m-$ is a linear perfluoroalkyl group;

m is an integer in the range between 2 and about 20, provided that the mixture contains at least 5 weight percent of molecules in which m is 8 or higher or mixtures of the same, but in no more than 5 weight percent of the molecules is m equal to 14 or higher or mixtures of the same;

n is an integer in the range between 1 and 3; and p is an integer in the range between 1 and about 40, provided that the distribution of molecules in said mixture has an average p in the range between 1 and 17;

said process comprising reacting ethylene oxide with a perfluoroalkylalkanol in accordance with the following equation:

$$F(CF_2)_m(CH_2)_nOH + p\ CH_2\!\!-\!\!\overset{O}{\!\!\!\frown\!\!\!}CH_2 \xrightarrow{\text{catalyst}} F(CF_2)_m(CH_2)_n(OCH_2CH_2)_pOH$$

wherein the catalyst consists essentially of a mixture of an alkali metal borohydride and at least one source of iodine selected from elemental iodine, alkali metal iodides, and alkaline earth metal iodides; and m, n, and p are as defined above.

6. The process of claim 5 where n is 2.

7. The process of claim 5 wherein the average of p in the molecular distribution of the mixture is in the range between about 12 and about 17.

8. The process of claim 7 wherein n is 2.

9. The process of either claim 5, 6, 7, or 8 wherein said source of iodine is elemental iodine.

10. The process of either claim 5, 6, 7, or 8 wherein said source of iodine is sodium iodide.

11. The process of either claim 5, 6, 7, or 8 wherein said source of iodine is a mixture of elemental iodine and sodium iodide.

* * * * *